(12) United States Patent
Harrison et al.

(10) Patent No.: US 8,900,607 B1
(45) Date of Patent: *Dec. 2, 2014

(54) CLEAR, GREASELESS SKIN-CARE COMPOSITIONS

(75) Inventors: James Jeffries Harrison, West Hills, CA (US); Nohemi Harrison, West Hills, CA (US)

(73) Assignee: Chemsil Silicones, Inc., Chatsworth, CA (US)

( * ) Notice: Subject to any disclaimer, the term of this patent is extended or adjusted under 35 U.S.C. 154(b) by 1424 days.

This patent is subject to a terminal disclaimer.

(21) Appl. No.: 10/855,934

(22) Filed: May 26, 2004

Related U.S. Application Data

(63) Continuation-in-part of application No. 10/254,418, filed on Sep. 25, 2002.

(51) Int. Cl.
*A61Q 19/00* (2006.01)
*A61K 8/67* (2006.01)
*A61K 31/07* (2006.01)
*A61K 8/89* (2006.01)

(52) U.S. Cl.
USPC ........... 424/401; 424/70.12; 514/63; 514/725

(58) Field of Classification Search
CPC ..... A61K 2300/00; A61K 8/89; A61K 8/585; A61Q 19/00; A61Q 19/02; A61Q 19/007
See application file for complete search history.

(56) References Cited

U.S. PATENT DOCUMENTS

| | | | |
|---|---|---|---|
| 4,608,392 A | 8/1986 | Jacquet et al. | |
| 4,888,363 A * | 12/1989 | Dulak et al. | 514/725 |
| 4,935,224 A | 6/1990 | Russo et al. | |
| 4,997,853 A | 3/1991 | Bernstein | |
| 5,013,726 A | 5/1991 | Ivy et al. | |
| 5,082,661 A * | 1/1992 | Melnik et al. | 424/401 |
| 5,124,320 A | 6/1992 | Ivy et al. | |
| 5,607,980 A * | 3/1997 | McAtee et al. | 514/476 |
| 5,759,529 A | 6/1998 | LeGrow et al. | |
| 5,856,361 A | 1/1999 | Holt et al. | |
| 5,916,548 A | 6/1999 | Hutchins et al. | |
| 5,993,837 A | 11/1999 | Calello et al. | |
| 6,103,266 A | 8/2000 | Tapolsky et al. | |
| 6,106,820 A | 8/2000 | Morrissey et al. | |
| 6,124,490 A | 9/2000 | Gormley et al. | |
| 6,296,880 B1 | 10/2001 | Murad | |
| 6,338,855 B1 | 1/2002 | Albacarys et al. | |
| 6,348,501 B1 | 2/2002 | Holt et al. | |
| 6,372,234 B1 | 4/2002 | Deckers et al. | |
| 6,383,523 B1 | 5/2002 | Murad | |
| 6,384,023 B2 | 5/2002 | Singleton et al. | |
| 6,403,069 B1 | 6/2002 | Chopra et al. | |
| 6,406,683 B1 | 6/2002 | Drechsler et al. | |
| 6,419,913 B1 | 7/2002 | Niemiec et al. | |
| 6,503,517 B1 * | 1/2003 | Mohammadi et al. | 424/401 |

* cited by examiner

*Primary Examiner* — Lakshmi Channavajjala
(74) *Attorney, Agent, or Firm* — Stout, Uxa & Buyan, LLP; Carlos A. Fisher

(57) ABSTRACT

The present invention relates to compositions including anhydrous compositions which include dimethicone crosspolymer and/or dimethicone elastomer gum and one or more skin care products which may include retinoic acid, retinoic acid derivatives, retinal, retinol and/or retinyl esters.

21 Claims, No Drawings

CLEAR, GREASELESS SKIN-CARE COMPOSITIONS

RELATED APPLICATION

This is a continuation-in-part of co-pending U.S. patent application Ser. No. 10/254,418, filed Sep. 25, 2002, the disclosure of which is hereby incorporated herein in its entirety by reference.

FIELD OF THE INVENTION

The present invention relates to clear, greaseless compositions which include a pharmaceutically active component. The compositions are preferably anhydrous and include silicones, for example, one or more of dimethicone crosspolymers, dimethicone gum, hexamethyldisiloxane and low molecular weight dimethicones.

More particularly, the composition may be a topically applied composition containing one or more analgesics or one or more skin care components.

In a further and more specific aspect, the invention relates to clear, greaseless compositions including a pharmaceutically active component such as an analgesic including methyl salicylate, camphor, menthol and capsaicin or a skin care component selected from the group consisting of anti-wrinkle components, anti-skin atrophy components, skin repair components, and mixtures thereof. Advantageously, the pharmaceutically active component is a skin care component selected from the group consisting of retinoic acid, retinoic acid derivatives, retinal, retinol, retinyl esters and mixtures thereof.

BACKGROUND

Various pharmaceutical products are designed for topical application, for instance in the form of gels, creams and lotions. Among such products are compositions including anti-acne actives, antimicrobial and antifungal actives, anti-wrinkle and anti-skin atrophy actives, skin barrier repair aids, cosmetic soothing aids, artificial tanning agents and accelerators, skin lightening actives, sunscreen actives, skin tightening agents, anti-itch agents, hair growth inhibitors, desquamating agents, anti-glycation agents, wound healing actives, actives to treat psoriasis, skin cancer, impetigo, herpes, chickenpox and dermatitis and mixtures thereof.

Some of the above compositions include components that are insoluble or only slightly soluble in water, but are readily soluble in non-polar substances such as organic solvents and oils. However, compositions including oils and the like have certain drawbacks in their use. For example, they may produce a sticky and/or greasy feel upon application to the skin. The compositions may also be inconvenient for use by, for example, requiring an extended drying time after application to the skin and/or staining the skin and/or clothing. In addition, these compositions do not necessarily provide for a film layer that will be effective to retain volatile actives. Further, after application the compositions typically are easily solubilized by aqueous solutions such as perspiration which may lead to loss of the composition and/or the actives. Further, water or oil containing compositions often include emulsifiers which can cause skin irritation. In addition, the process of making these compositions typically involves heating which may lead to the loss of the actives by, for example, evaporation and/or sublimation.

Two classes of pharmaceutical compositions particularly prone to the aforementioned drawbacks are skin-care compositions and analgesics.

Of special interest in the category of skin care compositions are compositions including anti-wrinkle components, anti-skin atrophy components, skin repair components and mixtures thereof, and particularly skin care compositions selected from the group consisting of retinoic acid, retinoic acid derivatives, retinal, retinol, retinyl esters and mixtures thereof.

Retinol, perhaps the most well known of these compositions, is frequently used in anti-aging creams, lotions, and serums. Because retinol is very unstable to heat, light, and oxygen, products containing retinol currently must be manufactured under inert gas conditions and packaged in aluminum tubes to prevent oxygen or light from degrading the active retinol. These restrictive manufacturing and packaging conditions increase the overall cost of the skin-care products, making them unaffordable to many consumers.

Also of interest are analgesic compositions, particularly compositions selected from the group consisting of methyl salicylate, camphor, menthol and capsaicin. Methyl salicylate is a 2-hydroxybenzoic acid methyl ester which can occur naturally in wintergreen oil, *betula* oil, sweet birch oil, teaberry oil and in the leaves of *Gualtheria procumbens* L. Ericadeae and in the bark of *Betula lenta* L. Betulaceae. It can also be prepared by etherification of salicylic acid with methanol. Camphor is 1,7,7-trimethylbicyclo[2,2,1]heptan-2-one and occurs in all parts of the camphor tree, *Cinnamomum camphora* T. It is also synthesized from vinyl chloride and cyclopentadiene. Menthol, or 5-methyl-2-[1-methylethyl]-cyclohexanol, can be obtained from mint oils, for example, peppermint oil. It can also be obtained through hydrogenation of thymol. Capsaicin, or N-(4-hydroxy-3-methoxybenzyl)-8-methylnontrans-6-enamide, can be obtained from the fruits of plants of the *Capsicum* genus.

Water and oil containing compositions such as gels, lotions and creams are useful for application of menthol, camphor, and capsaicin and methyl salicylate as well as other analgesics. U.S. Pat. No. 5,124,320 and U.S. Pat. No. 5,013,726 disclose compositions in which methyl salicylate, menthol and camphor are dissolved into C12-C15 alcohols benzoate, *eucalyptus* oil and jojoba oil.

There remains a need for topically applied compositions which may be used to apply skin-care products and/or analgesics which are easily and economically prepared, are non-sticky, greaseless, require less drying time after application to the skin, do not stain the skin, provide water resistance or waterproofing, act to efficiently retain actives and are not irritating to the skin.

In addition, a need exists for skin-care products, particularly retinol-containing skin-care products, which can be economically packaged in opaque containers and which remain stable when exposed to oxygen and/or higher than normal temperatures.

SUMMARY

The present invention meets these needs. Compositions of the invention can be manufactured at relatively low cost under non-restrictive conditions. Such compositions are preferably anhydrous with no oily component, and as such have a reduced greasy feel relative to similar or identical compositions which include oil and/or water. Advantageously, the compositions will dry in a reduced period of time relative to similar or identical compositions which include oil and/or water. In addition, the compositions may be made at room temperature which decreases the loss of certain actives during production. Moreover, the applied composition has increased resistance to being washed off or rubbed off, and has greater adhesion to the skin relative to aqueous or oil based compositions. Further, these compositions can provide a water resistant or water proof film when applied to a surface, for example, when applied to the skin. This water resistance or water proofing can prevent an undesired removal of actives upon exposure to moisture thereby retaining the active component in proximity to the surface (e.g. skin) to which the composition is applied. The water resistance or water proofing may be provided, at least in part, by a silicone component, which may include dimethicone gum and/or dimethicone crosspolymer, included in a composition.

In one broad embodiment, the present invention provides for an effective amount of a pharmaceutically active component to be included in a silicone component which may include a low molecular weight silicone (e.g., hexamethyldisiloxane and/or low molecular weight dimethicone) and a high molecular weight silicone (e.g., dimethicone crosspolymer and/or dimethicone elastomer gum). The high molecular weight silicone may be present in an amount effective to produce a composition with a desired consistency.

In one embodiment, the present invention provides for an anhydrous composition which includes a dimethicone crosspolymer and/or a dimethicone gum and an analgesic component. The dimethicone crosspolymer may have a molecular weight of between about 100,000 and about 100,000,000. The dimethicone gum may have a molecular weight of between about 100,000 and about 100,000,000. In still another embodiment, a composition includes the dimethicone crosspolymer and the dimethicone gum. In one embodiment, the dimethicone crosspolymer and/or dimethicone gum comprises about 10% to about 99.999% by weight of the composition.

In a particularly useful embodiment, the compositions include a low molecular weight silicone. Examples of low molecular weight silicones that may be included in a composition include, without limitation, low molecular weight dimethicone, cyclic silicones, and hexamethyldisiloxane.

The compositions may include a skin-care component selected from the group consisting of anti-wrinkle components, anti-skin atrophy components, skin repair components, and mixtures thereof. The skin care component is advantageously selected from the group consisting of retinoic acid, retinoic acid derivatives, retinal, retinol, retinyl esters and mixtures thereof. The skin care component may comprise about 0.0001% to about 1% or about 5% or about 10% by weight of the composition. In a particularly useful embodiment, the skin care component comprises about 0.0001% or about 0.01% or about 0.1% to about 0.3% to about 0.4% or 0.5% or about 1%, by weight of the composition.

Alternatively, the compositions may include an analgesic component which includes one or more analgesics. Examples of analgesics which may be included in the present compositions include camphor, menthol, capsaicin and methyl salicylate and mixtures thereof. The analgesic may comprise about 0.001% to about 90% of the composition by weight.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present invention is based in part upon the discovery of clear, greaseless silicone-containing compositions which may be anhydrous and include a pharmaceutically active component. The present invention also includes methods of making and using such compositions.

In one embodiment, the invention relates to compositions which include one or more of dimethicone crosspolymers, dimethicone gum, hexamethyldisiloxane and low molecular weight dimethicones. The active component may include one or more analgesics to treat pain. Particularly useful analgesics which may be included in a composition include, without limitation, methyl salicylate, camphor, menthol and capsaicin.

Particularly useful embodiments of the present composition include one or more of methyl salicylate menthol, camphor and capsaicin. In one embodiment, the active component includes methyl salicylate, menthol, camphor and capsaicin. In another embodiment, the active component includes menthol, camphor and capsaicin. In another embodiment, the active component includes camphor and capsaicin. In another embodiment, the active component includes capsaicin. In another embodiment, the active component includes camphor. In another embodiment, the active component includes menthol. In another embodiment, the active component includes methyl salicylate. In another embodiment, the active component includes methyl salicylate and camphor. In another embodiment, the active component includes methyl salicylate and menthol. In another embodiment, the active component includes methyl salicylate, camphor and capsaicin. In another embodiment, the active component includes methyl salicylate and capsaicin. In another embodiment, the active component includes menthol, and capsaicin. In another embodiment, the active component includes methyl salicylate, menthol and capsaicin. In another embodiment, the active component includes methyl salicylate menthol and camphor.

These and other embodiments of the present invention are effective to provide relief from pain by topical application to an animal patient, for example, topical application to a human patient, for example, application to the skin of a human patient. Without wishing to limit the invention to any theory or mechanism of operation, it is believed that these analgesics can relieve pain in areas of a body including, but not limited to, the skin, muscles, joints, or viscera distal to the site of application by stimulating depressing cutaneous sensory receptors.

Additional analgesics which may be included in a composition include, without limitation, salicylic acid, salicylic acid derivatives such as triethanolamine salicylate, histamine dihydrochloride, methyl nicotinate and wintergreen, *eucalyptus* and turpentine extracts as well as other counter irritants.

The active component may also include topical anesthetics such as pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol. Also included for use in the present compositions may be antipruritic drugs which include, without limitation, pharmaceutically-acceptable salts of methdilizine and trimeprazine.

Also included in an active component may be non-steroidal anti-inflammatory drugs (NSAIDS). The NSAIDS can be selected from the following categories: propionic acid derivatives; acetic acid derivatives; fenamic acid derivatives; biphenylcarboxylic, acid derivatives; and oxicams. All of these NSAIDS are described in the U.S. Pat. No. 4,985,459, which is incorporated in its entirety by reference herein. Propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Active ingredients useful herein may be categorized by their therapeutic benefit or their postulated mode of action such as analgesics, for example, topical analgesics. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Furthermore, pharmaceutically-acceptable salts of these active ingredients are also useful in accordance with the invention.

Other classes of active ingredients contemplated for use in the present compositions include anti-acne actives, antimicrobial and antifungal actives, anti-wrinkle and anti-skin atrophy actives, skin barrier repair aids, cosmetic soothing aids, artificial tanning agents and accelerators, skin lightening actives, sunscreen actives, skin tightening agents, anti-itch agents, Hair growth inhibitors, desquamating agents, anti-glycation agents, wound healing actives, actives to treat psoriasis, skin cancer, impetigo, herpes, chickenpox and dermatitis and mixtures thereof.

Anti-Acne Actives:

Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, for example, N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids and bioflavonoids; bile salts such as scymnol sulfate and its derivatives, deoxycholate, and cholate; abietic acid; adapalene; allantoin; aloe extracts; arbietic acid and its salts; aryl-2,4 dioxo oxazolidine derivatives; ASEBIOL (available from Laboratories Serobiologiques, located in Somerville, N.J.); azaleic acid; barberry extracts; bearberry extracts; *belamcanda chinensis*; benzoquinolinones; benzoyl peroxide; berberine; BIODERMINE (available from Sederma, located in Brooklyn, N.Y.); bioflavinoids; bisabolol; S-carboxymethyl cysteine; carrot extracts; cassin oil; clove extracts; citral; citronellal; climazole; Completech MBAC-OS (available from Lipo); CREMOGEN M82 (available from Dragoco, located in Totowa, N.J.); cucumber extracts; dehydroacetic acid and its salts; dehydroeplandersterone salicylate; dichlorophenyl imidazoldioxolan which is commercially available as COMPLETECH MBAC-OS (from Lipo, located in Paterson, N.J.); DL valine and its esters; DMDM hydantoin; Epicutin TT (available from CLR); erythromycin; escinol; ethyl hexyl monoglyceryl ether; ethyl 2-hydroxy undecanoate; farnesol; farnesol acetate; geranoil; glabridin; gluconic acid; gluconolactone; glyceryl monocaprate; glycolic acid; grapefruit seed extract; gugu lipid; Hederagenin (available from Maruzen); hesperitin; hinokitol; hops extract; hydrogenated rosin; 10 hydroxy decanoic acid; ichtyhol; interleukin 1 alpha antagonists; iodo-2-propynyl butyl carbamate; Kapilarine (available from Greentech); ketoconazole; lactic acid; lemon grass oil; Lichochalcone LR15 (available from Maruzen); linoleic acid; LIPACIDE C8CO (available from Seppic, located in Paris, France); lovastatin; 4 methoxysalicylic acid; metronidazole; minocycline; mukurossi; neem seed oil; vitamin B3 compounds (such as niacinamide and nicotinic acid); nisin; 5-octanoly salicylic acid; octopirox; panthenol; 1-pentadecanol; peonia extract; peppermint extract; phelladendron extract; 2-phenyl-benzothiophene derivatives; phloretin; PHLOROGINE (available from Secma); phosphatidyl choline; proteolytic enzymes; quercetin; red sandalwood extract; resorcinol; rosemary extract; rutin; sage extract; salicin; salicylic acid; skull cap extract; siber hegner extract; siberian saxifrage extract; silicol; sodium lauryl sulfate; sodium sulfoacetamide; *Sophora* Extract (available from Maruzen); sorbic acid; sulfur; sunder vati extract; tea tree oil; tetracyline; tetra hydroabietic acid; thyme extract; tioxolone; tocopherol; trehalose 6-undecylenoate; 3 tridecene-2-ol; triclosan; tropolone; UNITRIENOL T27 (available from Unichem, located in Gouda, Netherlands); vitamin $D_3$ and its analogs; white thyme oil; willow bark extract; wogonin; Ylang Ylang; zinc glycerolate; zinc linoleate; zinc oxide; zinc pyrithione; zinc sulfate and mixtures thereof.

Antimicrobial and Antifungal Actives:

Antimicrobial and antifungal actives can be effective to prevent the proliferation and growth of bacteria and fungi. Nonlimiting examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentarnidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; *arnica* extract (helenalin acetate and 11,13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; *capsicum frutescens* extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydrofarnesol; dehydroacetic acid and its salts; dill seed oil;

DOWICIL 200 (available from Dow Chemical, located in Midland, Mich.); *echinacea*; elenolic acid; epimedium; ethyl paraben; Fo—Ti; *galbanum*; garden bumet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; 1,6 hexanediol; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume; mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propyl paraben; purslane; quillaira; rhubarb; rose geranium oil; rosemary; sage; salicylic acid; *sassafras*; savory; sichuan lovage; sodium meta bisulfite; sodium sulfite; SOPHOLIANCE (available from Soliance, located in Compiegne, France); sorbic acid and its salts; sphingosine; *stevia*; storax; sucrose esters; tarmic acid; tea; tea tree oil (cajeput oil); thyme; triclosan; triclocarban; tropolone; turpentine; umbelliferone (antifungal); *yucca*; and mixtures thereof.

Anti-Wrinkle, Anti-Skin Atrophy and Skin Repair Actives:

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include retinoic acid and its derivatives (e.g., cis and trans); retinal; retinol; retinyl esters such as retinyl acetate, retinyl palmitate, and retinyl propionate; vitamin B compounds (such as niacinamide and nicotinic acid), salicylic acid and derivatives thereof (such as 5-octanoyl salicylic acid, heptyloxy 4 salicylic acid, and 4-methoxy salicylic acid); sulfur-containing D and L amino acids and their derivatives and salts, particularly the N-acetyl derivatives, for example, N-acetyl-L-cysteine; thiols, e.g. ethane thiol; hydroxy acids, phytic acid, lipoic acid; lysophosphatidic acid; skin peel agents (e.g., phenol and the like); Actein 27-Deoxyactein Cimicifugoside (available from Cirnigoside); adapalene; ademethionine; adenosine; aletris extract; alkyl glutathione esters; alkoxyalkoxy alkoxyn benzoic and derivatives; aloe derived lectins; amino propane phosphoric acid; 3-aminopropyl dihydrogen phosphate; Amadorine (available from Barnet Products); anise extracts; AOSINE (available from Secma); arginine amino benzoate; ASC III (available from E. Merck, located in Darmstadt, Germany); ascorbic acid; ascorbyl palmitate; asiatic acid; asiaticosides; ARLAMOL GEO™ (available from IC, located in Wilmington, Del.); azaleic acid; benzoic acid derivatives; Bertholletia extracts; betulinic acid; BIOCHANIN A AND BIOPEPTIDE CL (available from Sederma, located in Brooklyn, N.Y.); BIOPEPTIDE EL (available from Sederma); biotin; blackberry bark extract; blackberry lily extracts; black cohosh extract; blue cohesh extract; butanoyl betulinic acid; carboxymethyl 1,3 beta glucan; catecholamnines; chalcones; citric acid esters; chaste tree extract; clover extracts; coumestrol; CPC Peptide (available from Barnet Products); daidzein; dang gui extract; darutoside; debromo laurinterol; 1-decanoyl-glycero-phosphonic acid; dehydrocholesterol; dehydrodicreosol; dehydrodieugenol; dehydroepiandersterone; DERMOLECTINE (available from Sederma); dehydroascorbic acid; dehydroepiandersterone sulfate; dianethole; dihydroxy benzoic acid; 2,4 dihydroxybenzoic acid; diglycol guanidine succinate; diosgenin; disodium ascorbyl phosphate; dodecanedioic acid; Ederline (available from Seporga); Enderline (available from Laboratories Seporga); equol; eriodictyol; estrogen and its derivatives; ETF (available from Laboratories Seporga); ethocyn; ELESERYL SH (available from Laboratories Serobiologiques, located in Somerville, N.J.); ENDONUCLEINE (available from Laboratories Serobiologiques); ergosterol; eythrobic acid; fennel extract; fenugreek seed extract; FIBRASTIL (available from Sederma); FIBROSTIMULINES S and P (available from Sederma); FIRMOGEN LS 8445 (available from Laboratories Serobiologiques); formononetin; forsythia fruit extract; gallic acid esters; gamma amino butyric acid; GATULINE RC (available from Gattlefosse, located in Priest, France); genistein; genisteine; genistic acid; gentisyl alcohol; gingko bilboa extracts; *ginseng* extracts; ginsenoside; gluco pyranosyl-L-ascorbate; glutathione and its esters; glycitein; hesperitin; hexahydro curcumin; HMG—coenzyme A reductase inhibitors; hops extracts; 11 hydroxy undecanoic acid; 10 hydroxy decanoic acid; 25-hydroxycholesterol; 7-hydroxylated sterols; hydroxyethyl isostearyloxy isopropanolamine; hydroxy-tetra methyl piperidinyloxy; hypotaurine; ibukijakou extract; isoflavone SG 10 (available from Barnet Products); kinetin; kohki extract; L-2-OXO-thiazolidine-4-carboxylic acid esters; lactate dehydrogenase inhibitors; 1-lauryl, -lyso-phosphatidyl choline; lectins; lichochalcone LF15 (available from Maruzen); licorice extracts; lignan; lumisterol; lupenes; luteolin; lysophosphitidic acid; magnesium ascorbyl phosphate; margin; melatonin; melibiose; metalloproteinase inhibitors; methoprene; methoprenic acid; mevalonic acid; MPC COMPLEX (available from CLR); N methyl serine; N methyl taurine; N, N.sup.1-bis(lactyl) cysteamine; naringenin; neotigogenin; o-desmethylangoiensin; oat beta glucan; oleanolic acid; pantethine; phenylalanine; photoanethone; piperdine; placental extracts; pratensein; pregnenolone; pregnenolone acetate; pregnenolone succinate; premarin; quillaic acid; raloxifene; REPAIR FACTOR 1 and REPAIR FACTOR FCP (both available from Sederma); retinoates (esters of C2-C20 alcohols); retinyl glucuronate; retinyl linoleate; S-carboxymethyl cysteine; SEANAMINE FP (available from Laboratories Serobiologiques); sodium ascorbyl phosphate; soya extracts; spleen extracts; tachysterol; taurine; tazarotene; tempol; thymulen; *thymus* extracts; thyroid hormones; tigogenin; tocopheryl retinoate; toxifolin; traumatic acid; tricholine citrate; trifoside; uracil derivatives; ursolic acid; vitamin D.sub.3 and its analogs; vitamin K; vitex extract; yam extract; yamogenin; zeatin; and mixtures thereof.

Skin Barrier Repair Actives:

Skin barrier repair actives are those skin care actives which can help repair and replenish the natural moisture barrier function of the epidermis. Nonlimiting examples of skin barrier repair actives include Alpha Lipid (available from Lucas Meyer); ascorbic acid; biotin; biotin esters; brassicasterol; caffeine; campesterol; canola derived sterols; Cennamides (available from Ennagram); Ceramax (available from Alban Muller); CERAMAX (available from Quest, located in Ashford, England); CERAMIDE 2 and CERAMIDE HO3™ (both available from Sederma); CERAMIDE II (available from Quest); CERAMIDE III and IIIB (both available from Cosmoferm, located in Deft, Netherlands); CERAMIDE LS 3773 (available from Laboratories Serobiologiques); CERAMINOL (available from Inocosm); Cerasol and Cephalip (both available from Pentapharm); cholesterol; cholesterol hydroxystearate; cholesterol isostearate; 7 dehydrocholesterol; DERMATEIN BRC and DERMATEIN GSL (both available from Hormel); ELDEW CL 301 AND ELDEW PS 203 (both available from Ajinomoto); Fitobroside (available from Pentapharm); galactocerebrosides; Generol 122 (available from Henkel); glyceryl serine amide; hydroxyethyl isostearyl isopropanolamine; lactic acid; Lactomide (available from Pentapharm); lanolin; lanolin alcohols; lanosterol; lauric acid N laurylglucamide; lipoic acid; N-acetyl cysteine; N-acetyl-L-serine; N-methyl-L-Serine; Net Sterol-ISO (available from Barnet Products); vitamin B3 compounds (such as niacinamide and nicotinic acid); palmitic acid; panthenol; panthetine; phosphodiesterase inhibitors; PHYTO/CER (available from Intergen); phytoglycolipid millet extract (available from Barnet Products Distributer, located in Englewood, N.J.); PHYTOSPHINGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; sphingomylinase; S-lactoyl glutathione; stearic acid; Structurine (available from Silah); SUPER STEROL ESTERS (available from Croda); thioctic acid; THSC CERAMIDE OIL (available from Campo Research); trimethyl glycine; tocopheryl nicotinate; vitamin D.sub.3; Y2 (available from Ocean Pharmaceutical); and mixtures thereof.

Non-Steroidal Cosmetic Soothing Actives:

Cosmetic soothing actives can be effective in preventing or treating inflammation of the skin. The soothing active enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency. Nonlimiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Nonlimiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, *absinthium, acacia,* aescin, alder buckthorn extract, allantoin, aloe, APT (available from Centerchem), *arnica,* astragalus, astragalus root extract, azulene, Baicalin SR 15 (available from Barnet Products Dist.), baikal skullcap, baizhu, balsam canada, bee pollen, BIOPHYTEX (available from Laboratories Serobiologiques), bisabolol, black cohosh, black cohosh extract blue cohosh, blue cohosh extract, boneset, borage, borage oil, bradykinin antagonists, bromelain, *calendula, calendula* extract, Canadian Willowbark Extract (available from Fytokem), candelilla wax, Cangzhu, canola phytosterols, *capsicum,* carboxypeptidase, celery seed, celery stem extract, *CENTAURIUM* (available from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (available from Croda), darutoside, dehurian *angelica,* devil's claw, divalent metals (such as, magnesium, strontium, and manganese), doggrass, dogwood, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, feverfew, ficin, forsythia fruit, Fytosterol 85 (available from Fytokem), *ganoderma,* gaoben, Gatuline A (available from Gattefosse), gentian, germanium extract, gingko bilboa extract, ginkgo, *ginseng* extract, goldenseal, gorgonian extract, gotu kola, grape fruit extract, guaiac wood oil, guggal extract, helenalin esters, henna, honeysuckle flower, horehound extract, horsechestnut, horsetail, huzhang, *hypericum,* ichthyol, immortelle, ipecac, job's tears, jujube, kola extract, LANACHRYS 28 (available from Lana Tech), lemon oil, lianqiao, licorice root, *ligusticum, ligustrum,* lovage root, luffa, mace, *magnolia* flower, manjistha extract, margaspidin, matricin, melatonin, MICROAT IRC (available from Nurture), mints, mistletoe, Modulene (available from Seporga), mono or diglucosides of glabridin, mono or diglucosides of gentisin, MTA (5'-deoxy-5'-methythioadenosine), mung bean extract, musk, N-methyl arginine, oat beta glucan, oat extract, orange, panthenol, papain, phenoxyacetic acid, peony bark, peony root, Phytoplenolin (available from Bio Botanica), phytosphingosine, Preregen (available from Pentapharm), purslane, QUENCH T (available from Centerchem), quillaia, red sage, rehmannia, rhubarb, rosemary, rosmarinic acid, royal jelly, rue, rutin, sandlewood, sanqi, sarsaparilla, saw *palmetto,* SENSILINE (available from Silab), SIEGESBECKIA (available from Sederma), stearyl glycyrrhetinate, Stimutex (available from Pentapharm), storax, strontium nitrate, sweet birch oil, sweet woodruff, *tagetes,* tea extract, thyme extract, tienchi *ginseng,* tocopherol, tocopheryl acetate, triclosan, turmeric, urimei, ursolic acid, white pine bark, witch hazel xinyi, yarrow, yeast extract, *yucca,* and mixtures thereof.

Artificial Tanning Actives and Accelerators.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; acetyl tyrosine; phospho-DOPA; brazilin; caffeine; coffee extracts; dihydroxyacetone; DNA fragments; isobutyl methyl xanthine; methyl xanthine; Phototan (available from Laboratoires Serobiologiques); prostaglandins; tea extracts; theophylline; tyrosine; UNIPERTAN P2002 and UNIPERTAN P27 (both available from Unichem); and mixtures thereof.

Skin Lightening Actives:

Skin lightening actives can actually decrease the amount of melanin in the skin or provide such an effect by other mechanisms. Skin lightening actives suitable for use herein are described in copending patent application Ser. No. 08/479,935, filed on Jun. 7, 1995 in the name of Hillebrand, corresponding to PCT Application No. U.S. Ser. No. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. Ser. No. 95/02809, filed Mar. 1, 1995, published Sep. 8, 1995; all incorporated herein by reference. Nonlimiting examples of skin lightening actives useful herein include adapalene, aloe extract, alpha-glycaryl-L-ascorbic acid, aminotyroxine, ammonium lactate, anethole derivatives, apple extract, arbutin, *areca catechu* L. extract, ascorbic acid, ascorbyl palmitate, azelaic acid, bamboo extract, bearberry extract, bletilla tuber, bupleurum falcatum extract, burnet extract, Burnet Power (available from Barnet Products), butyl hydroxy anisole, butyl hydroxy toluene, butyl resoreinol, Chuanxiong, cola decaballo extract, Dang-Gui, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, esculoside, esculetin, FADEOUT (available from Pentapharm), Fangfeng, fennel extract, gallic acid and its derivatives, ganodenna extract, gaoben, GATULINE WHITENING (available from Gattlefosse), genistic acid and its derivatives, gentisyl alcohol, glabridin and its derivatives, gluco pyranosyl-1-ascorbate, gluconic acid, glucosamine, glycolic acid, glycyrrhizinic acid, green tea extract, 4-Hydroxy-5-methyl-3[2H]-furanone, hydroquinine, 4 hydroxyanisole and its derivatives, 4-hydroxy benzoic acid derivatives, hydroxycaprylic acid, hyptis extract, inositol ascorbate, kojic acid, kojic dipalnitate, lactic acid, lemon extract, licorice extract, Licorice P-TH (available from Barnet Products), linoleic acid, magnesium ascorbyl phosphate, Melfade (available from Pentapharm), MELAWHITE (available from Pentapharm), Melanostatine DM (available from Laboratories Seporga), *morus alba* extract, mulberry root extract, niacinamide, 5-octanoyl salicylic acid, parsley extract, *phellinus linteus* extract, pinon blanco extract, pinon negro extract, *piri-piri* extract, pyrogallol derivatives, retinoic acid, retinol, retinyl esters (acetate, propionate, palmitate, linoleate), 2,4 resorcinol derivatives, 3,5 resorcinol derivatives, rose fruit extract, rucinol, salicylic acid, Song-Yi extract, *Sophora* Powder (available from Barnet Products), 4-thioresorein, 3,4,5 trihydroxybenzyl derivatives, tranexamic acid, tyrostat (*Rumex* Extract available from Fytokem), Tyroslat 10,11 (available from Fytokem), vanilla derivatives, vitamin D.sub.3 and its analogs, and mixtures thereof.

Sunscreen Actives:

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N, N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Still other useful sunscreens include aminobenzoic acid (PABA), benzylidene camphor, butyl methoxy dibenzoyl methane, diethanolamine p-methoxycinnamate, dioxybenzone, ethyl dihydroxypropyl (PABA), glyceryl aminobenzoate, homomenthyl salicylate, isopropyl dibenzoyl methane, lawsone and dihydroxyacetone, menthyl anthranilate, methyl anthranilate, methyl benzylidene camphor, octocrylene, octyl dimethyl (PABA), octyl methoxycinnamate, oxybenzone, 2-phenylbenzimidazole-5-sulfonic acid, red petrolatum, sulisobenzone, titanium dioxide, triethanolamine salicylate, zinc oxide, and mixtures thereof. Examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Exact amounts of sunscreens which can be employed will vary depending upon the sunscreen chosen and the desired Sun Protection Factor (SPF) to be achieved. SPF is a commonly used measure of photoprotection of a sunscreen against erythema. See Federal Register, Vol. 43, No. 166, pp. 38206-38269, Aug. 25, 1978, which is incorporated herein by reference in its entirety.

Skin Tightening Agents:

Also useful as active ingredients in the present invention are skin tightening agents. Nonlimiting examples of skin tightening agents which are useful in the compositions of the present invention are those selected from the group consisting of Biocare SA (available from Amerchol); egg albumen; Flexan 130 (available from National Starch); Gatuline Lifting (available from Gattefosse); Pentacare HP (available from Pentapharm); Vegeseryl (available from Laboratories Serobioloques) and mixtures thereof.

Anti-Itch Ingredients:

Also useful as active ingredients in the present invention are anti-itch ingredients. Nonlimiting examples of anti-itch ingredients which are useful in the compositions of the present invention are those selected from the group consisting of Stimu-tex (available from Pentapharm); Takanal (available from Ikeda-Distributer); Ichthyol (available from International Sourcing-Distributor); Oxygenated Glyceryl Triesters (available from Seporgia) and mixtures thereof.

Hair Growth Inhibitors:

Nonlimiting examples of hair growth inhibitors which are useful in the compositions of the present invention include 17-beta estradiol, adamantyguanidines, adamantylamidines, adenylosuccinate synthase inhibitors, anti angiogenic steroids, aspartate transcarbamylase inhibitors, betamethasone valerate, bisabolol, copper ions, *curcuma* extract, cycloxygenase inhibitors, cysteme pathway inhibitors, dehydroacetic acid, dehydroepiandrosterone, diopyros leak extract, epidermal growth factor, epigallocatechin, essential fatty acids, evening primrose oil, gamma glutamyl transpeptidase inhibitors, ginger oil, glucose metabolism inhibitors, glutamine metabolism inhibitors, glutathione, green tea extracts, heparin, Kapilanne (available from International Sourcing Distributor), L, 5 diaminopentanoic acid, L-aspargine synthase inhibitors, linoleic acid, lipoxygenase inhibitors, *longa* extract, mimosinamine dihydrochloride, mimosine, nitric oxide synthase inhibitors, non-steroidal antiinflamatories, ornithine decarboxylase inhibitors, omthine aminotransferase inhibitors, panthenol, phorhetur, phosphodiesterase inhibitors, pleione extract, protein kinase C inhibitors, salpha reductase inhibitors, sulfhydral reactive compounds, tioxolone, transforming growth factor beta 1, urea, zinc ions and mixtures thereof.

Desquamating Enzyme Enhancers:

Nonlimiting examples of desquamating enzyme enhancers which are useful in the compositions of the present invention include alanine, aspastic acid, N methyl serine, serine, trimethyl glycine and mixtures thereof.

Anti-Glycation Agents:

A nonlimiting example of an anti-glycation agent which is useful in the compositions of the present invention would be Amadorine (available from Barnet Products Distributor).

Other useful actives include skin bleaching (or lightening) actives including but not limited to hydroquinone, ascorbic acid, kojic acid and sodium metabisulfite.

Other useful actives include antiperspirant actives. Suitable for use herein are those which comprise any compound, composition or mixture thereof having antiperspirant activity. Astringent metallic salts are antiperspirant materials for use herein, for example, the inorganic and organic salts of aluminum, zirconium and zinc, as well as mixtures thereof. Non-limiting examples are the aluminum and zirconium salts, such as aluminum halides, aluminum hydroxy halides, zirconyl oxide halides, zirconyl hydroxy halides, and mixtures thereof.

Additionally, deodorant actives in the form of bacteriostats may be incorporated into the present compositions. Suitable deodorant bacteriostats include 2,2'-methylenebis(3,4,6-trichlorophenol), 2,4,4'-trichloro-2'-hydroxy(diphenyl ether), zinc phenolsulfonate, 2,2'-thiobis(4,6-dichlorophenol), p-chloro-m-xylenol, dichloro-m-xylenol and the like. One example is 2,4,4'-trichloro-2'-hydroxy(diphenyl ether), which is generically known as triclosan and available from the Ciba-Geigy Corporation under the trademark, Irgasan DP-300 Registered™. When triclosan is utilized it will be present in a range from about 0.05 to about 0.9%, for example, from about 0.1 to about 0.5% (weight %) of the composition. Other types of bacteriostats include sodium N-lauroyl sarcosine, sodium N-palmitoyl sarcosine, lauroyl sarcosine, N-myristoyl glycine, potassium N-lauroyl sarcosine and aluminum chlorhydroxy lactate (sold by Reheis Chemical Company under trademark of Chloracel).

Based on a weight percentage, the active component may be present in a composition in a range of about 0.0001% to about 60.0%, for example, about 0.005% to about 50% (weight %). In one embodiment, methyl salicylate, menthol, camphor and capsaicin are each present in a composition in a range of about 0.0001% to about 60%. For example, methyl salicylate may be present in a range of about 0.1% to about 40.0% (weight percentage), for example, about 0.5% to about 30%; menthol may be present in a range of about 0.1% to about 20%, for example, about 0.5% to about 16%; camphor may be present in range of about 0.1% to about 20%, for example, about 0.5% to about 6%; and capsaicin may be present in a range of about 0.0001% to about 5.0% weight percentage, for example, about 0.002% to about 0.01%.

Some or all of the substances (e.g., analgesic active(s)) which may be included in a composition may be dissolved in a silicone material. In one embodiment, some or all of the substances (e.g., analgesic active(s)) which are included in a composition are dissolved in one or more low molecular weight silicones. In another embodiment, one or more of the substances (e.g., analgesic active(s)) which are included in a composition are dissolved in an organic solvent and then added to the silicone material. For example, capsaicin may be dissolved in a C12-C15 alkyl benzoate and then added to the silicone material which comprises a composition. In weight percent, about 3% to about 15% (weight % of composition), for example, about 7% to about 15% of alkyl benzoate can be used to dissolve capsaicin.

Organic compounds useful in the present composition include, without limitation, inert aromatic hydrocarbons, aliphatic hydrocarbons, alcohols, aldehydes, ketones, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, isoparaffinic solvents and mineral spirits; alkyl halides such as chloroform, carbon tetrachloride, perchloroethylene, ethylchloride and chlorbbenzene; aromatic hydrocarbons such as benzene, toluene, ethybenzene and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether and propylene glycol monophenyl ether; ketones such as acetone, methyl ethyl ketone, cyclohexanone, diacetone alcohol, methyl amyl ketone, and diisobutyl ketone.

Low molecular weight silicones useful in the present invention include volatile silicones. By volatile silicone it is meant a silicone material that has a measurable vapor pressure at ambient temperature, for example, silicones with a boiling point of about 250 degrees C. or less at about atmospheric pressure and with viscosities generally less than about 10 centistokes (CS) measured at twenty-five degrees C., for example, 0.65 to 5.0 centistokes.

Low molecular weight cyclic silicones such as cyclomethicones, for example, octylmethylcyclotetrasiloxane, hexamethylcyclotrisiloxane and decamethylcyclopentasiloxane and the like are contemplated for use in the present compositions. Low molecular weight linear silicones may also be useful, for example, polydimethylsiloxanes. Particularly useful low molecular weight silicones include hexamethyldisiloxane and low molecular weight dimethicone. Mixtures of these and other low molecular weight silicones are also within the scope of the invention.

The compositions may include low molecular weight silicone in a range of about 5% to about 95% (weight %), for example, about 30% to about 80%. In one embodiment, the compositions include about 35% to about 75% hexamethyldisiloxane and/or low molecular weight dimethicones.

Low molecular weight silicones including hexamethyldisiloxane and low molecular weight dimethicones are clear fluids, and are essentially odorless, nontoxic, nongreasy and nonstinging. These fluids are nonirritating to skin, and exhibit enhanced spreadability and ease of application to the skin.

Without wishing to limit the invention to any theory or mechanism of operation it is believed that after application of a present composition, the low molecular weight silicones substantially evaporate leaving behind some or all of the remainder of the composition which may include a high molecular weight silicone material. This high molecular weight silicone may have an average molecular weight in excess of 100,000 (e.g., between about 500,000 and about 5,000,000) and/or be non-volatile.

Examples of silicone polymers contemplated for use in the present compositions include, without limitation, copolymers such as stearyl methyl-dimethyl siloxane copolymer (Gransil SR-CYC, available from Grant Industries, Elmwood Park, N.J.); Polysilicone-11 (i.e., a crosslinked silicone rubber formed by the reaction of vinyl terminated silicone and methylhydrodimethyl siloxane in the presence of cyclomethicone), cetearyl dimethicone/vinyl dimethicone crosspolymer (i.e., a copolymer of cetearyl dimethicone crosslinked with vinyl dimethyl polysiloxane), dimethicone/phenyl vinyl dimethicone crosspolymer (i.e., copolymer of dimethylpolysiloxane crosslinked with phenyl vinyl dimethylsiloxane), and dimethicone/vinyl dimethicone crosspolymer (i.e., copolymer of dimethylpolysiloxane crosslinked with vinyl dimethylsiloxane). Particularly useful high molecular weight silicones include crosslinked siloxane, for example dimethicone crosspolymers or dimethicone derivative crosspolymers and silicone gums, for example, dimethicone elastomer gum.

In one particularly useful aspect of the present invention, the consistency of a composition is controlled by adding certain amounts of high molecular weight silicone polymers to the low molecular weight silicones. The viscosity range of the final compositions may be adjusted to about 0.1 CS to about 50,000 CS or about 10,000,000, for example, about 0.1 CS to about 3500 CS or about 0.5 CS to about 50 CS. One useful viscosity range for the present compositions may be about 0.65 CS to about 10 CS.

In one particularly useful embodiment, a dimethicone crosspolymer is employed in a composition and is effective to control the consistency of compositions. In another particularly useful embodiment, dimethicone gum is employed in a composition and is effective to control the consistency of compositions. In another particularly useful embodiment, dimethicone crosspolymers and/or dimethicone gum are employed in a composition and are effective to control the consistency of compositions. The viscosity of the crosspolymer employed may be about 1,000,000 or higher.

Advantageously, dimethicone crosspolymers and dimethicone gum do not have a greasy feel. In addition, these compositions can provide a water resistant or water proof film when applied to a surface, for example, when applied to the skin. This water resistance or water proofing can prevent an undesired removal of actives upon exposure to moisture. The film can also provide for moisture retention. The moisture retention may be effective to retain actives, for example, volatile actives, in proximity to the surface to which the composition is applied, for example, the skin.

The range of molecular weight of high molecular weight silicones, for example, dimethicone crosspolymers and dimethicone gum may be from about 100,000 to about 100,000,000, for example, about 500,000 to about 50,000,000 or about 1,000,000 to about 10,000,000.

The high molecular weight silicones, for example, dimethicone crosspolymers and dimethicone gum may be capped. Caps may be any suitable group including methyl groups, phenyl groups, hydroxy groups, vinyls and/or amino groups or mixtures or combinations thereof.

The compositions may include high molecular weight silicone in a range of about 5% to about 95% (weight %), for example, about 3% to about 30%. For example, a composition may include dimethicone crosspolymer and or dimethicone gum in a range of about 5% to about 25%.

A silicone component includes the silicone material which comprises a composition of the invention. In one broad embodiment, a composition of the invention includes a silicone component, which includes low molecular weight silicones and high molecular weight silicones present at a concentration in a range of between about 30% to about 99.999% (weight %), for example, about 40-99.9%.

In one embodiment, one or more of substances (e.g., analgesic active(s)) which are included in a composition of the invention are dissolved into the silicone component.

In certain embodiments, the present compositions can include additional substances including, without limitation, moisturizers, emollients, fragrances preservatives and sugars.

The compositions of the present invention can include one or more moisturizing materials. These materials include, but are not limited to, urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine: and mixtures thereof.

The compositions useful the present invention may also include one or more emollients. Examples of suitable emollients which may be useful in the present compositions include, but are not limited to, highly branched hydrocarbons, and non-polar carboxylic acid and alcohol esters, and mixtures thereof. Some emollients that may be useful in the present compositions are further described in U.S. Pat. No. 4,919,934, which is incorporated herein by reference in its entirety.

Examples of fragrances which may be useful in the present compositions include, without limitation, peppermint, rose oil, rose water, aloe vera, clove oil, *eucalyptus* oil, and other plant extracts. Certain fragrances may require a solubilizer, e.g., PPG-5-ceteareth-20. To eliminate certain odors from compositions, masking agents may be used. An example of a masking agent includes ethylene brassylate. Other fragrances and masking agents are listed on pages 1639-40 of the ICT Handbook.

Preservatives can be used to protect the compositions from degradation. Examples of preservatives which may be useful in the present compositions include, without limitation, liquipar oil, phenoxyethanol, methyl paraben, propyl paraben, butyl paraben, isopropyl paraben, isobutyl paraben, dieizolidinyl urea, imidazolidinyl urea, diazolindyl urea, benzalkonium chloride, benzethonium chloride, phenol, and mixtures thereof (e.g., liquipar oil). Other preservatives are listed on pages 1654-55 of the ICT Handbook.

Examples of sugars which may be useful in the present compositions include, without limitation, monosaccharides, disaccharides, and polysccharides such as glucose, xylose, fructose, reose, ribose, pentose, arabinose, allose, tallose, altrose, mannose, galactose, lactose, sucrose, erythrose, or any combination thereof.

The compositions of the present invention are used in conventional ways to provide a desired benefit. The present compositions can be used to provide, for example, pain relief (analgesic) by, for example, topical application to the skin. Methods of use depend upon the type of composition employed but, in one broad embodiment, involve application of an effective amount of the product to the skin which may then be allowed to remain on the skin. By "effective amount" is meant an amount sufficient to provide a benefit desired. For example, an effective amount of a composition is applied to and rubbed onto the skin.

Compositions of the invention may be substantially anhydrous allowing for application to the skin with no greasy feel. The compositions dry rapidly leaving behind a silicone polymer film with no oily residue that prevents evaporation or washing away of actives thereby retaining the active component in proximity to the surface of the skin to which the composition is applied.

The following non-limiting examples illustrate certain aspects of the present invention.

EXAMPLES

Percentages presented in the examples are weight percentages. A weight percentage is a percentage expressed as the percentage of the total composition based on weight.

Example 1

Methyl salicylate 30.0%
Menthol 10.0%
Camphor 4.0%

Low molecular weight dimethicone 45.0%
Dimethicone crosspolymer 11.0%

The methyl salicylate, menthol and camphor are dissolved in the low molecular weight dimethicone producing an admixture and the dimethicone crosspolymer is blended into the admixture.

Example 2

Methyl salicylate 15.0%
Menthol 7.5%
Camphor 2.5%
Hexamethyldisiloxane 61.0%
Dimethicone crosspolymer 14.0%

The methyl salicylate, camphor and/or menthol are dissolved in the hexamethyldisiloxane producing an admixture and the dimethicone crosspolymer is blended into the admixture.

Example 3

Methyl salicylate 5.0%
Menthol 1.0%
Camphor 2.0%
Capsaicin 0.075%
C12-C15 alkyl benzoate 16.925%
Hexamethyldisiloxane 61.0%
Dimethicone crosspolymer 14.0%

The capsaicin is dissolved in the alkyl benzoate and the methyl salicylate, menthol and camphor are dissolved in the hexamethyldisiloxane to which the capsaicin/alkyl benzoate solution is added producing an admixture. The dimethicone crosspolymer is blended into the admixture.

Example 4

Capsaican 0.1%
C12-C15 alkyl benzoate 15.9%
Low molecular weight dimethicone 70.0%
Dimethicone crosspolymer 14.0%

The capsaicin is dissolved in the alkyl benzoate. The capsaicin/alkyl benzoate solution and the methyl salicylate, menthol and camphor are added to the low molecular weight dimethicone producing an admixture and the dimethicone crosspolymer is blended into the admixture.

Example 5

Methyl salicylate 30.0%
Menthol 10.0%
Camphor 4.0%
Low molecular weight dimethicone 45.0%
Dimethicone elastomer gum 11.0%

The methyl salicylate, menthol and camphor are dissolved in the low molecular weight dimethicone producing an admixture and the dimethicone elastomer gum is blended into the admixture.

Example 6

Methyl salicylate 15.0%
Menthol 7.5%
Camphor 2.5%
Hexamethyldisiloxane 61.0%
Dimethicone elastomer gum 14.0%

The methyl salicylate, menthol and camphor are dissolved in the hexamethyldisiloxane producing an admixture and the dimethicone elastomer gum is blended into the admixture.

Example 7

Methyl salicylate 5.0%
Menthol 1.0%
Camphor 2.0%
Capsaicin 0.075%
C12-C15 alkyl benzoate 16.925%
Hexamethyldisiloxane 61.0%
Dimethicone elastomer gum 14.0%

The capsaicin is dissolved in the alkyl benzoate and the methyl salicylate, menthol and camphor are dissolved in the hexamethyldisiloxane to which the capsaicin/alkyl benzoate solution is added producing an admixture. The dimethicone elastomer gum is blended into the admixture.

Example 8

Capsaican 0.1%
C12-C15 alkyl benzoate 15.9%
Low molecular weight dimethicone 70.0%
Dimethicone elastomer gum 14.0%

The capsaicin is dissolved in the alkyl benzoate which is then added to the low molecular weight dimethicone producing an admixture. The dimethicone elastomer gum is blended into the admixture.

Example 9

Methyl salicylate 30.0%
Menthol 10.0%
Camphor 4.0%
Low molecular weight dimethicone 45.0%
Dimethicone crosspolymer 6.0%
Dimethicone elastomer gum 5.0%

The methyl salicylate, menthol and camphor are dissolved in the low molecular weight dimethicone producing an admixture and the dimethicone elastomer gum and dimethicone crosspolymer are blended into the admixture.

Example 10

Methyl salicylate 15.0%
Menthol 7.5%
Camphor 2.5%
Hexamethyldisiloxane 61.0%
Dimethicone crosspolymer 7.0%
Dimethicone elastomer gum 7.0%

The methyl salicylate, menthol and camphor are dissolved in the hexamethyldisiloxane producing an admixture and the dimethicone elastomer gum and dimethicone crosspolymer are blended into the admixture.

Example 11

Methyl salicylate 5.0%
Menthol 1.0%
Camphor 2.0%
Capsaicin 0.075%
C12-C15 alkyl benzoate 16.925%
Hexamethyldisiloxane 61.0%
Dimethicone crosspolymer 7.0%
Dimethicone elastomer gum 7.0%

The capsaicin is dissolved in the alkyl benzoate and the methyl salicylate, menthol and camphor are dissolved in the hexamethyldisiloxane to which the capsaicin/alkyl benzoate solution is added producing an admixture. The Dimethicone crosspolymer and dimethicone elastomer gum are blended into the admixture.

Example 12

Capsaican 0.1%
C12-C15 alkyl benzoate 15.9%
Low molecular weight dimethicone 70.0%
Dimethicone crosspolymer 7.0%
Dimethicone elastomer gum 7.0%

The capsaicin is dissolved in the alkyl benzoate and is added to the low molecular weight dimethicone producing an admixture. The dimethicone crosspolymer and dimethicone elastomer gum are blended into the admixture.

Example 13

Retinol-15D (a 15% solution of all trans 0.3%
retinol in caprylic/capric triglyceride,
stabilized with 1% BHT)
Low molecular weight dimethicone 80.0%
Dimethicone crosspolymer 19.7%

The Retinol-15D is dissolved in the low molecular weight dimethicone, producing an admixture, and the dimethicone crosspolymer is blended into the admixture using the cold mix process. The resulting composition is packaged in opaque high density polyethylene (HDPE) containers during the production processing and packaging. No inert gas is used. The compositions in these containers are tested and found to have no retinol degradation.

The containers are resealed and are then exposed to sunlight and probable higher than normal (room) temperatures, and retested after three months. After three months of such exposure, the compositions in the opaque containers are found to be optically clear, and to contain active retinol.

Similar tests are conducted except that the compositions are placed in clear polyethylene terephthalate (PET) containers and clear glass containers. Again, no inert gas is used during packaging. Upon retesting, after three months of exposure to sunlight and higher than normal temperatures, the compositions in the PET and glass containers are hazy and contain no active retinol.

Example 14

Retinol 15D (a 15% solution of all trans 0.3%
retinol in caprylic/capric triglyceride,
stabilized with 1% BHT)
Low molecular weight dimethicone 80.0%
Dimethicone gum 19.7%

The Retinol-15D is dissolved in the low molecular weight dimethicone, producing an admixture, and the dimethicone gum is blended into the admixture using the cold mix process. The resulting composition is packaged in opaque high density polyethylene (HDPE) containers under the same conditions as Example 13. After testing, the compositions in these containers are found to have no retinol degradation.

The containers are resealed and are then exposed to sunlight and probable higher than normal (room) temperatures, and retested after three months. After three months of such exposure, the compositions in the opaque containers are found to be optically clear, and to contain active retinol.

Similar tests are conducted except that the compositions are placed in clear polyethylene terephthalate (PET) containers and clear glass containers. Again, no inert gas is used during packaging. Upon retesting, after three months of exposure to sunlight and higher than normal temperatures, the compositions in the PET and glass containers are hazy and contain no active retinol.

These tests, as set forth in Exhibits 13 and 14, show that the present compositions, prepared by the cold mix process without the use of inert gases, are stable when exposed to oxygen and higher than normal temperatures, but unstable when exposed to light. Accordingly, such compositions preferably are to be packaged in opaque containers.

A number of publications, patents, and patent applications have been cited hereinabove. Each of the cited publications, patents, and patent applications are hereby incorporated by reference in their entireties.

While this invention has been described with respect to various specific examples and embodiments, it is to be understood that the invention is not limited thereto and that it can be variously practiced with the scope of the following claims.

What is claimed is:

1. An anhydrous composition comprising a high molecular weight silicone component having a molecular weight between 100,000 and about 100,000,000 daltons and a low molecular weight silicone component, said low molecular weight silicone component consisting essentially of a low molecular weight linear silicone component, and wherein said composition further comprises a soluble or solubilized active component selected from the group consisting of retinoic acid, retinoic acid derivatives, retinal, retinol, retinyl esters and mixtures thereof; wherein the active component has increased stability when the composition is stored in a container for three months relative to the stability of the active component in an otherwise identical composition in which a cyclic low molecular weight silicone component is substituted for the low molecular weight linear silicone component and is stored in an identical container for the same period of time.

2. The composition of claim 1 wherein the active component has increased stability when the composition is exposed to higher than room temperature.

3. The composition of claim 1 wherein the high molecular weight silicone component is a dimethicone gum is capped with one or more groups selected from the class consisting of methyl groups, hydroxyl groups, phenyl groups, vinyls, amino groups and mixtures thereof.

4. The composition of claim 1 wherein the low molecular weight silicone is selected from the class consisting of low molecular weight dimethicones.

5. The composition of claim 1 wherein the low molecular weight silicone comprises hexadimethylsiloxane.

6. The composition of claim 1 wherein the active component is selected from the group consisting of retinoic acid, retinol, and mixtures thereof.

7. The composition of claim 1 wherein the active component comprises retinol.

8. The composition of claim 1 wherein the active component comprises about 0.001% to about 10% by weight of the composition.

9. The composition of claim 1, wherein the anhydrous composition is disposed within an opaque package.

10. The composition of claim 1, wherein the active component comprises about 0.01% to about 0.5% by weight of the anhydrous composition.

11. An anhydrous composition comprising a high molecular weight dimethicone gum component having a molecular weight between 100,000 and about 100,000,000 daltons, a low molecular weight silicone component consisting essentially of a low molecular weight linear silicone component, and a soluble active component selected from the group consisting of retinoic acid, retinoic acid derivatives, retinal, retinol, retinyl esters, and mixtures thereof, wherein the active component has increased stability when the composition is stored for at least 30 days and exposed to oxygen, light, and/or room temperature relative to the stability of the same active component in an otherwise identical composition in which a cyclic low molecular weight silicone component is substituted for the low molecular weight linear silicone component and is stored for the same period of time and under the same conditions.

12. The composition of claim 11 wherein the low molecular weight silicone is selected from the class consisting of low molecular weight dimethicones.

13. The composition of claim 11 which further comprises hexadimethylsiloxane.

14. The composition of claim 11 wherein the active component is selected from the group consisting of retinoic acid, retinol and mixtures thereof.

15. The composition of claim 11 wherein the active component is retinol.

16. The composition of claim 11 wherein the active component comprises about 0.0001% to about 10% by weight of the composition.

17. An anhydrous composition comprising a dimethicone gum component having a molecular weight between 100,000 and about 100,000,000 daltons, a low molecular silicone component consisting essentially of a low molecular weight linear dimethicone having a measurable vapor pressure at 25° C., and a soluble or solubilized active component selected from the group consisting of retinoic acid, retinoic acid derivatives, retinal, retinol, retinyl esters and mixtures thereof; the dimethicone gum and the low molecular weight dimethicone being present in the composition in an amount in a range of about 40-99.9% by weight, the active component having increased stability when the composition is placed into a clear container and exposed to sunlight for about three months relative to the stability of the active component in an otherwise identical composition in which the low molecular weight component is a cyclic siloxane stored under identical conditions for an identical period of time.

18. The composition of claim 17, wherein the active component is selected from the group consisting of retinoic acid, retinol and mixtures thereof, and is present in an amount of about 0.0001% to about 10% by weight of the composition.

19. The composition of claim 17, wherein the active component is retinol.

20. An anhydrous composition comprising a dimethicone gum component having a molecular weight between 100,000 and about 100,000,000 daltons; a low molecular weight silicone component consisting essentially of a linear dimethicone having a measurable vapor pressure at 25° C.; and a soluble or solubilized active component selected from the group consisting of retinoic acid, retinoic acid derivatives, retinal, retinol, retinyl esters and mixtures thereof.

21. The composition of claim 20 wherein said low molecular weight linear dimethicone is selected from the group consisting of a dimethicone and hexamethyldisiloxane.

* * * * *